(12) United States Patent
Rotstein

(10) Patent No.: US 9,610,404 B2
(45) Date of Patent: Apr. 4, 2017

(54) METHOD FOR OCCLUSION DETECTION FOR AN INFUSION PUMP SYSTEM

(71) Applicant: Bigfoot Biomedical, Inc., Milpitas, CA (US)

(72) Inventor: Yaron Rotstein, Sunnyvale, CA (US)

(73) Assignee: Bigfoot Biomedical, Inc., Milpitas, CA (US)

(*) Notice: Subject to any disclaimer, the term of this patent is extended or adjusted under 35 U.S.C. 154(b) by 47 days.

(21) Appl. No.: 14/461,678

(22) Filed: Aug. 18, 2014

(65) Prior Publication Data

US 2015/0005736 A1    Jan. 1, 2015

Related U.S. Application Data

(62) Division of application No. 13/226,689, filed on Sep. 7, 2011, now Pat. No. 8,808,230.

(51) Int. Cl.
*A61M 5/168* (2006.01)
*A61M 5/14* (2006.01)
(Continued)

(52) U.S. Cl.
CPC ........ *A61M 5/16831* (2013.01); *A61M 5/142* (2013.01); *A61M 5/1413* (2013.01);
(Continued)

(58) Field of Classification Search
CPC ...... A61M 5/16831; A61M 2205/3306; A61M 2205/3313; A61M 2005/16863;
(Continued)

(56) References Cited

U.S. PATENT DOCUMENTS

| 4,924,870 A | * | 5/1990 | Wlodarczyk | ......... G01L 9/0077 |
| | | | | 600/480 |
| 5,172,112 A | * | 12/1992 | Jennings | ............. E21B 47/0001 |
| | | | | 166/336 |

(Continued)

FOREIGN PATENT DOCUMENTS

| CA | 2543545 | 5/2005 |
| DE | 196 27 619 | 1/1998 |

(Continued)

OTHER PUBLICATIONS

Accu-Chek Spirit, "Pump Therapy Made for You," Roche, 2006, 6 pages.

(Continued)

*Primary Examiner* — Theodore Stigell
*Assistant Examiner* — Benjamin Koo
(74) *Attorney, Agent, or Firm* — Fish & Richardson P.C.

(57) ABSTRACT

Some embodiments of an infusion pump system include an occlusion detection system to detect when an occlusion exists in the fluid path between the medicine reservoir and the infusion site located, for example, on the user's skin. The occlusion detection system can be configured to self-calibrate in a manner that accounts for changes in environmental conditions, such as ambient temperature, pressure, or the like, so that the occlusion detection system provides reliable feedback to a user as to the occluded or non-occluded state of the medicine flow path.

12 Claims, 14 Drawing Sheets

(51) Int. Cl.
*A61M 5/145* (2006.01)
*A61M 39/28* (2006.01)
*A61M 5/142* (2006.01)

(52) U.S. Cl.
CPC .... *A61M 5/14248* (2013.01); *A61M 5/14566* (2013.01); *A61M 5/16854* (2013.01); *A61M 39/284* (2013.01); *A61M 2005/14268* (2013.01); *A61M 2005/16863* (2013.01); *A61M 2205/3306* (2013.01)

(58) Field of Classification Search
CPC ......... A61M 2005/16868; A61M 2005/16872; A61M 5/16854; A61M 5/16859; G01L 9/0077
See application file for complete search history.

(56) References Cited

U.S. PATENT DOCUMENTS

| | | | |
|---|---|---|---|
| 5,225,763 A | 7/1993 | Krohn et al. |
| 5,858,001 A | 1/1999 | Tsals et al. |
| 6,436,072 B1 | 8/2002 | Kullas et al. |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Mahoney et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe |
| 7,789,859 B2 | 9/2010 | Estes et al. |
| 7,917,312 B2 * | 3/2011 | Wang ..................... G01F 1/661 702/45 |
| 2001/0041869 A1 | 11/2001 | Causey, III et al. |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |

(56) References Cited

U.S. PATENT DOCUMENTS

| | | |
|---|---|---|
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0239116 A1 | 10/2007 | Follman et al. |
| 2008/0051716 A1 | 2/2008 | Stutz |
| 2008/0097381 A1 | 4/2008 | Moberg et al. |
| 2008/0208627 A1 | 8/2008 | Skyggebjerg |
| 2008/0294094 A1* | 11/2008 | Mhatre ............... A61M 5/1413 604/65 |
| 2008/0319383 A1 | 12/2008 | Byland et al. |
| 2009/0118667 A1 | 5/2009 | Haueter et al. |
| 2010/0274216 A1* | 10/2010 | Wade ................... A61M 5/142 604/500 |

FOREIGN PATENT DOCUMENTS

| | | |
|---|---|---|
| DE | 102 36 669 | 2/2004 |
| EP | 0 062 974 | 10/1982 |
| EP | 0 496 141 | 7/1992 |
| EP | 0 612 004 | 8/1994 |
| EP | 0 580 723 | 10/1995 |
| EP | 0 275 213 | 7/1998 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/068015 | 9/2002 |
| WO | WO 02/084336 | 10/2002 |
| WO | WO 02/100469 | 12/2002 |
| WO | WO 03/026726 | 4/2003 |
| WO | WO 03/074121 | 9/2003 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |
| WO | WO 2007/141786 | 12/2007 |

OTHER PUBLICATIONS

Authorized Officer Jacques Voinot, International Search Report and Written Opinion for Application No. PCT/US2012/053912, dated Nov. 26, 2012, 10 pages.

Collins and Lee, "Microfluidic flow transducer based on the measurement of electrical admittance," *Lab Chip*, 2004, 4:7-10.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

International Preliminary Report on Patentability in International Application No. PCT/US2012/053912, mailed Mar. 20, 2014, 7 pages.

International Preliminary Report on Patentability in International Application No. PCT/US2008/064244, mailed Dec. 3, 2009, 9 pages.

International Search Report & Written Opinion, PCT/US2008/064244, mailed Sep. 16, 2008, (17 pages).

Medtronic News Release, "Medtronic Receives FDA Approval for World's First Insulin Pump with Real-time Continuous Glucose Monitoring," Apr. 13, 2006, 3 pages.

OmniPod Insulin Management System-Investor Relations—Press Release, Feb. 1, 2005, http://investors.insulet.com/phoenix/zhtml?c=209336&p=irol-newsArticle&ID=988708&highlight= 1 page.

OmniPod Quick Start Guide, 2007, 2 pages.

Patent Abstracts of Japan, vol. 1999, No. 04, and JP 11 010036, Apr. 30, 1999 and Jan. 19, 1999, Toray Ind. Inc.

The Medtronic Diabetes Connection, 2006, 6 pages.

Xilas Temp Touch, "The latest in high-tech and convenient devices," DOCNews, vol. 2, No. 7, Jul. 1, 2005, http://docnews.diabetesjournals.org/cgi/content/full/2/7/13, 3 pages.

\* cited by examiner

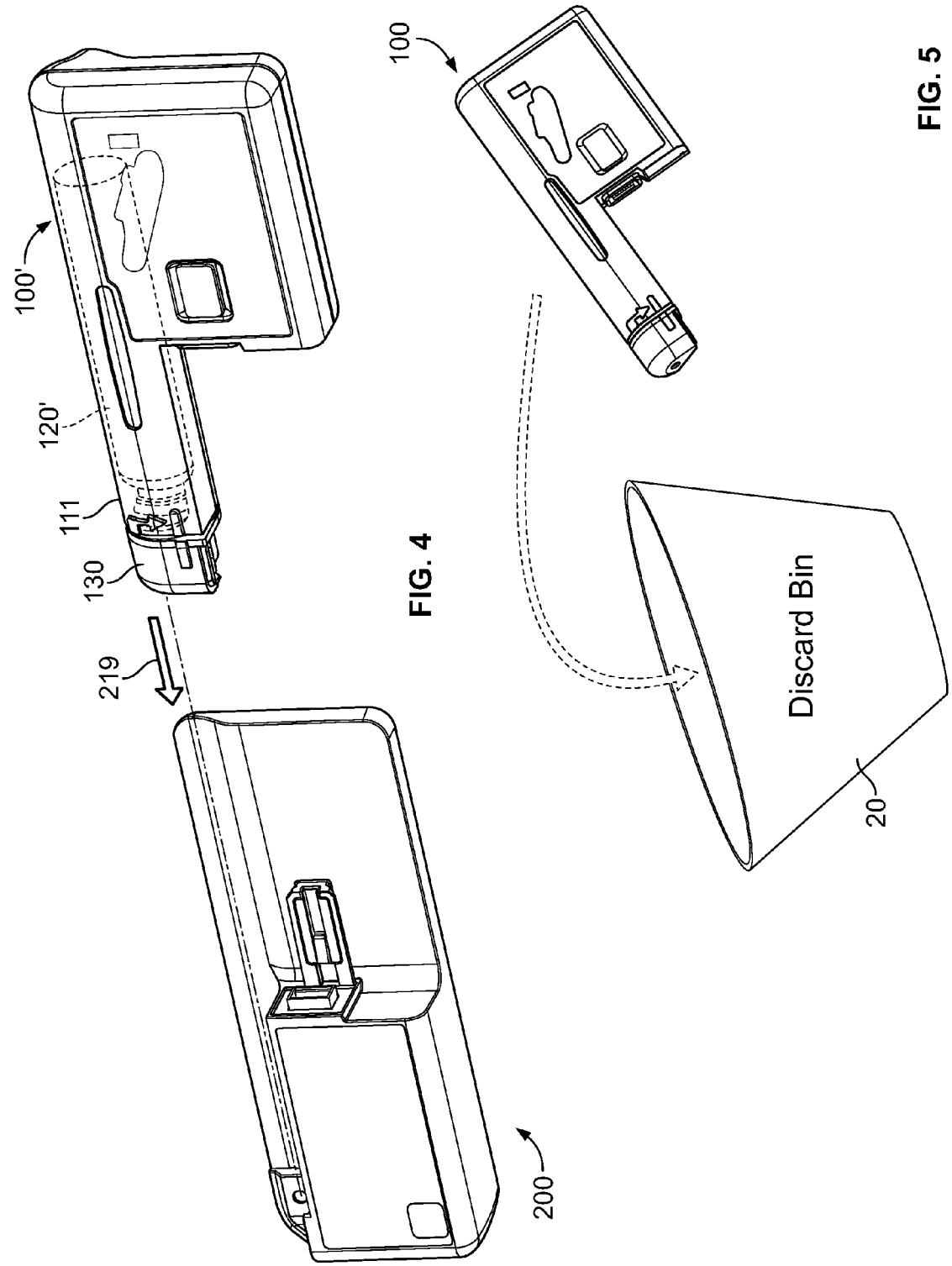

METHOD FOR OCCLUSION DETECTION FOR AN INFUSION PUMP SYSTEM

CLAIM OF PRIORITY

This is a divisional application and claims priority under 35 USC §119(e) to U.S. patent application Ser. No. 13/226,689, filed on Sep. 7, 2011, now U.S. Pat. No. 8,808,230, the entire contents of which are hereby incorporated by reference.

TECHNICAL FIELD

This document relates to an infusion pump system, such as a portable infusion pump system for dispensing insulin or another medication.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Some traditional infusion pump devices may include an occlusion detection system for purposes of determining when the medicine dispensation is inadvertently interrupted or interfered. If the medicine dispensation path to the user is occluded, the user may receive no dosage or a lower dosage of the medicine. Some occlusion detections systems for infusion pumps can be configured as a "dry side" detector in which a sensor is positioned along a component of the drive system to detect a malfunction or change in pressure. Other occlusion detection systems for infusion pumps can be configured as a "wet side" detector in which characteristics of the fluid flow path are monitored. In some circumstances, the occlusion detection systems may be sensitive to environmental conditions (e.g., ambient temperature, pressure, or the like) in a manner that could cause false indications of a flow path occlusion.

SUMMARY

Some embodiments of an infusion pump system include an occlusion detection system to detect when an occlusion exists in the fluid path between the medicine reservoir and the infusion site located, for example, on the user's skin. Such an occlusion may occur, for example, when the fluid flow line (e.g., a cannula, infusion set tubing, or the like) is kinked. The occlusion detection system can be configured to account for changes in environmental conditions, such as ambient temperature, pressure, or the like, so that the occlusion detection system provides reliable feedback to a user as to the occluded or non-occluded state of the medicine flow path. As such, the occlusion sensor can be used to indicate when the fluid is flowing or not flowing, thereby permitting the infusion pump system to communicate an alarm to the user if an occlusion exists.

Particular embodiments described herein include an occlusion sensor system for detecting an occlusion in a flow path from an insulin infusion pump system. The occlusion sensor system may include a fluid channel that at least partially defines an insulin flow path between an insulin reservoir and an output port. The system may also include a flexible membrane in fluid communication with the fluid channel so that fluid pressure in the fluid channel acts upon the flexible membrane. The system may further include an air cavity positioned adjacent to the flexible membrane and generally opposite the fluid channel. The system may include a light transmissive member adjacent to the air cavity. The light transmissive member may be arranged opposite the flexible membrane such that fluid pressure in the fluid channel above a threshold value causes the flexible membrane to deform into the air cavity and toward the light transmissive member. The system may also include a primary light emitter configured to align with the light transmissive member and emit light into the light transmissive member. The system may further include a light sensor configured to align with the light transmissive member and receive light from the primary light emitter that passes through the light transmissive member. The system may include a reference light emitter configured to emit light that is received by the light sensor, wherein the reference light emitter is spaced apart from the primary light emitter.

Some embodiment described herein may include occlusion sensor system for an infusion pump system including a reusable controller device that is removably attachable to a disposable single-use pump device that defines a space to receive medicine therein. The occlusion sensor system may include a primary light emitter, a reference light emitter, and a light sensor arranged in the reusable controller device. The primary light emitter, the reference light emitter, and the light sensor may be in electrical communication with control circuitry housed inside the reusable controller device. The system may also include a light transmissive member arranged in the disposable single-use pump device. The light transmissive member may be aligned with the primary light emitter and the light sensor when the reusable controller device is removably attached to a disposable single-use pump device. The light sensor may be positioned relative to the light transmissive member so as to receive light from the primary light emitter that passes through the light transmissive member in response to activation of the primary light emitter. Also, in response to activation of the reference light emitter, the light sensor may receive light emitted from the reference light emitter without passing through the light transmissive member.

Particular embodiments described herein may include an occlusion sensor system for detecting an occlusion in a flow path from an insulin infusion pump system. The occlusion sensor system may include a primary light emitter configured to emit light toward an insulin flow path. The system may also include a light sensor configured to receive at least a portion of the light from the primary light emitter after the light is emitted toward the insulin flow path. The light sensor may output an electrical signal in response to receiving light. The system may further include a reference light emitter configured to emit light that is received by the light sensor. The reference light emitter may be separate from the primary light emitter. The system may further include control circuitry electrically connected to the primary light emitter, the reference light emitter, and the light sensor. The control circuitry may compare a first value indicative of light detected at the light sensor from the primary light emitter to a second value indicative of light detected at the light sensor from the reference light emitter. In response to the comparison of the first value to the second value being outside of a threshold range, the control circuitry may generate an occlusion alarm for output via a user interface.

Some embodiments include a method for detecting an occlusion in a flow path from an infusion pump system. The method may include activating a reference light emitter to direct light toward a light sensor housed in an infusion pump system. The light sensor may generate an electrical signal in response to receiving light from the reference light emitter. The method may also include determining a first value indicative of light detected at the light sensor from the reference light emitter. The method may further include activating a primary light emitter to direct toward a medicine flow path for the infusion pump system. The light sensor may receive a least a portion of the light emitted from the primary light emitter. The method may include determining a second value indicative of light detected at the light sensor from the primary light emitter. The method may also include determining if an occlusion exists in the medicine flow path based at least in part on a comparison of the second value to the first value.

Some or all of the embodiments described herein may provide one or more of the following advantages. First, the infusion pump system may include an occlusion detection system configured to reliably detects occlusions in the medicine flow path even when the infusion pump system is exposed to significant changes in environments conditions. For example, the occlusion detection system can be configured to self-calibrate and thereby account for changes in ambient temperature so that the occlusion detection system provides reliable feedback even when the infusion pump system is carried in low-temperature conditions. As such, the occlusion detection system can provide notice to the user if he or she is receiving no dosage or a lower dosage of the medicine due to an occlusion in the medicine flow path.

Second, particular embodiments of the occlusion detection system may employ at least two different light emitters for each light sensor. For example, the occlusion detection system may include a primary light emitter that emits a light for communication toward the medicine flow path and is received at a light detector (e.g., after internal reflection of the light). In addition, the occlusion detection system may include a reference light emitter that emits a light for communication along a different path toward the light detector. As such, a comparison of the detected light signal from the reference light emitter and the detected light signal from the primary light emitter can be employed to calibrate the occlusion detection system to account for changes in environmental conditions.

Third, some embodiments of the infusion pump system may include a reusable controller device that houses the electronic components of the occlusion detection system even though the electronic components of the occlusion sensor system are used to detect characteristics the medicine flow path passing through a removable pump device. As such, sensor signals of the occlusion detection system can be readily communicated to control circuitry of the reusable controller device to determine if an occlusion exists. If so, the user interface of the controller device can be used to promptly alert the user of the problem.

Fourth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

Like reference symbols in the various drawings indicate like elements.

DETAILED DESCRIPTION OF ILLUSTRATIVE EMBODIMENTS

Figure 1:
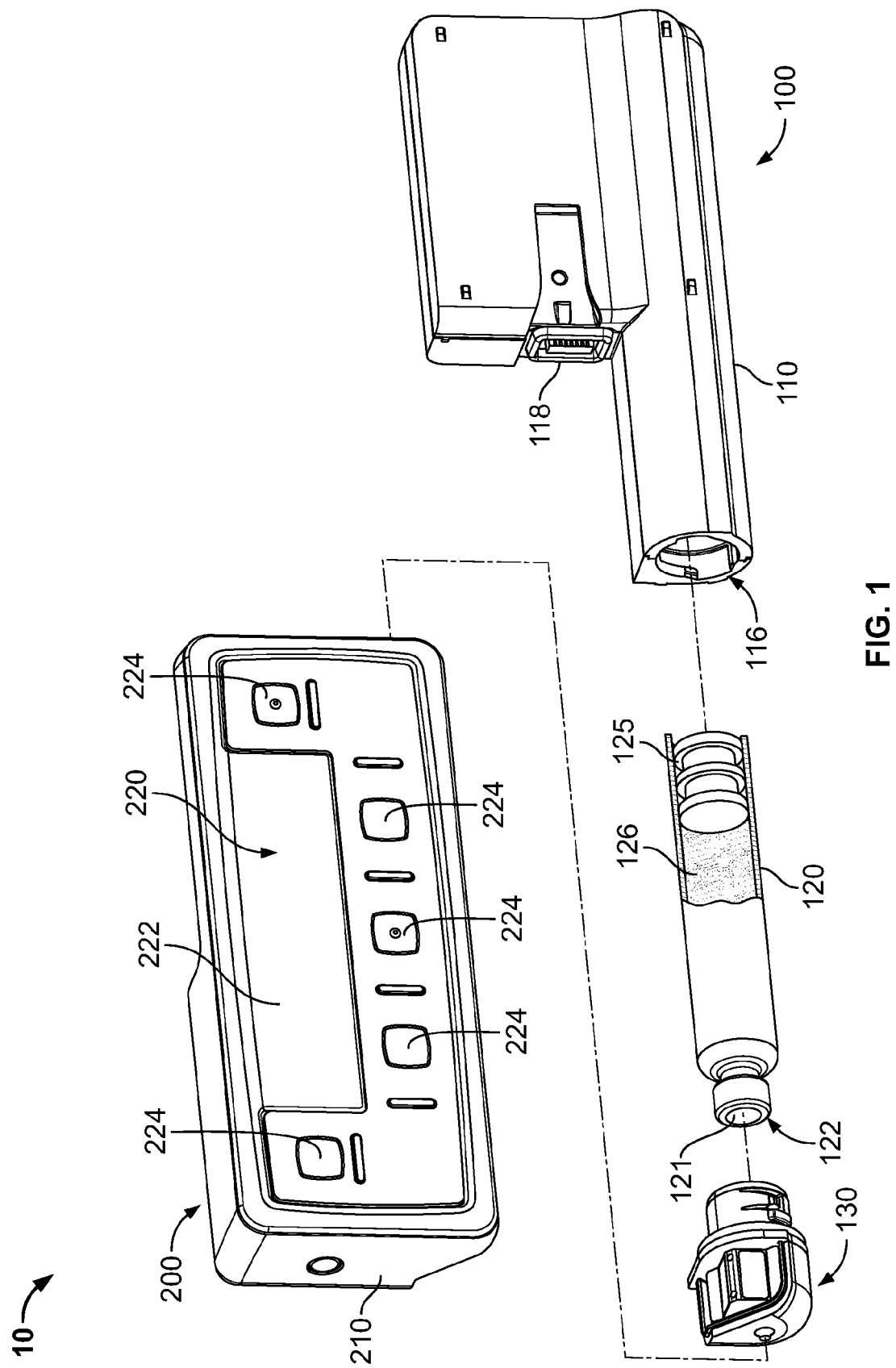
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system that advances a plunger 125 in the fluid cartridge 120 so as to dispense fluid therefrom. As described in more detail below in connection with FIGS. 8-16, the pump system can include an occlusion detection system 250 that is advantageously configured to self-calibrate in a manner that accounts for changes in environmental conditions, such as ambient temperature, pressure, or the like. As such, the occlusion detection system 250 may provide reliable feedback to a user as to the occluded or non-occluded state of the medicine flow path extending between the fluid cartridge 120 and the infusion site.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3).

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 6) of the controller device 200 and from the power source 310 (refer to FIG. 7) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

Figure 2:
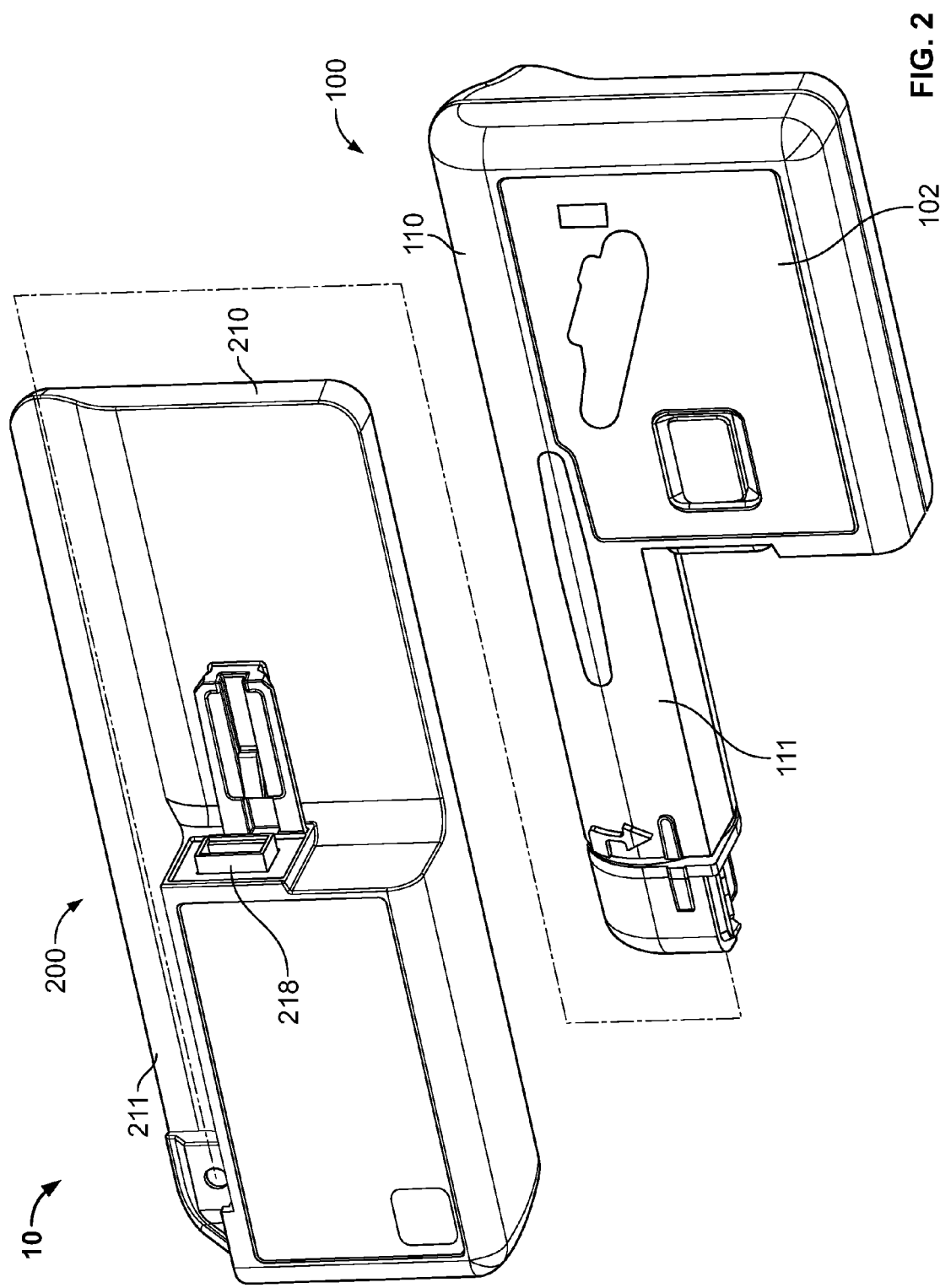
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 3:
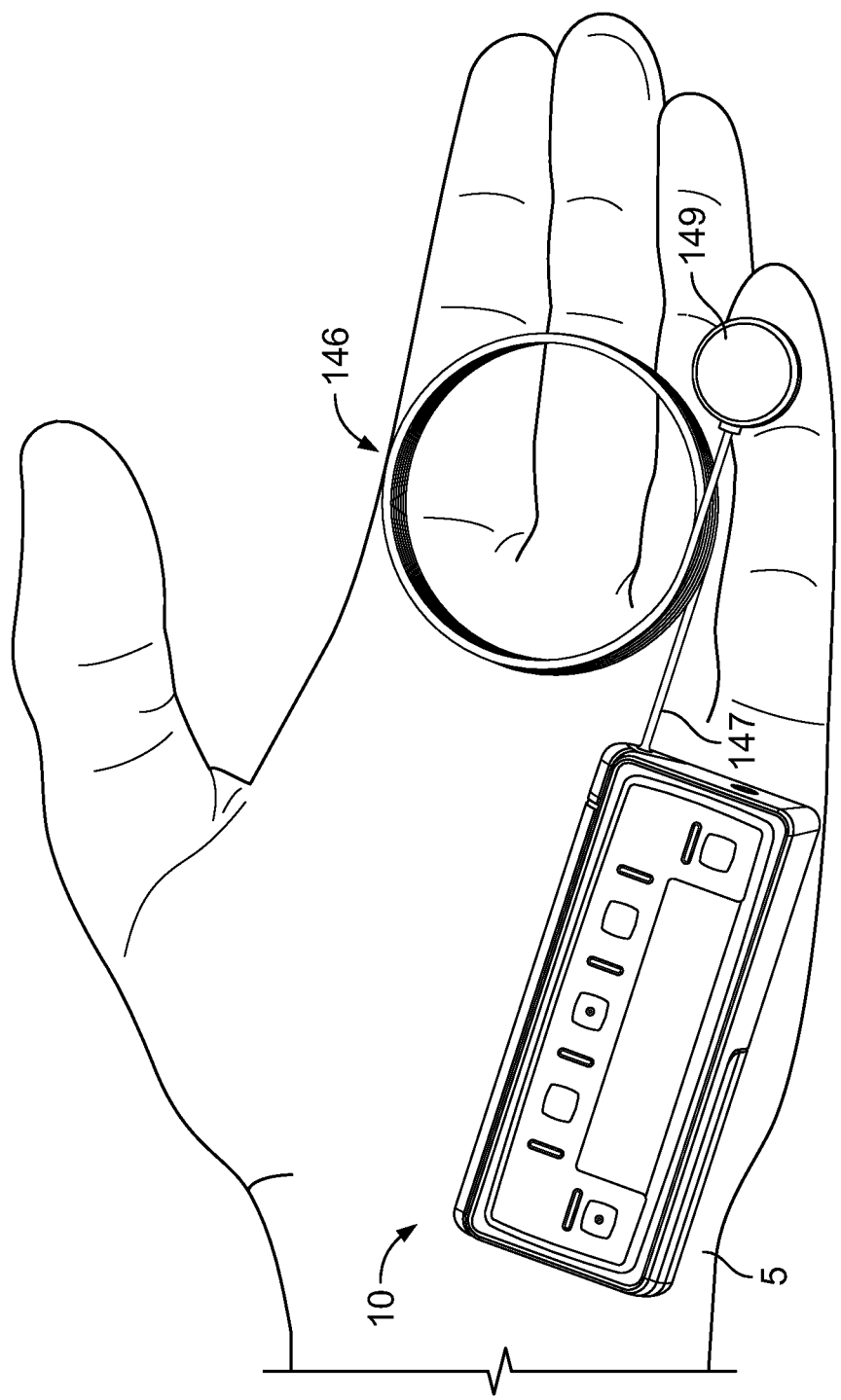
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin) The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 6:
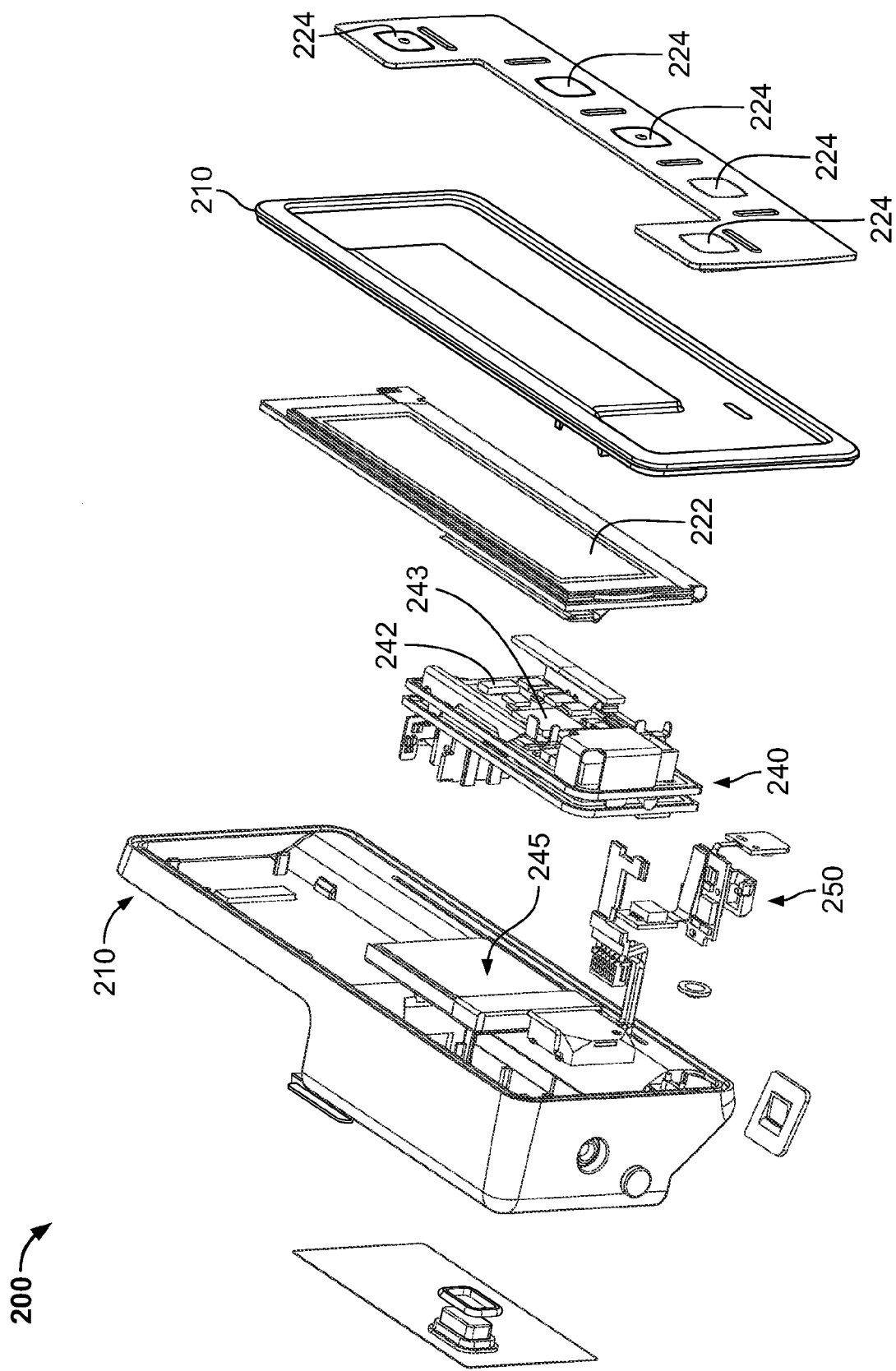
FIG. 6 is an exploded perspective view of a controller device for an infusion pump system, in accordance with some embodiments.

Referring now to FIG. 6, the controller device 200 (shown in an exploded view) houses a number of components that can be reused with a series of successive pump devices 100. In particular, the controller device 200 can include controller circuitry 240 and a rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or to components of the pump device 100. Controller circuitry 240 may be configured to communicate control or power signals to the drive system of the pump device 100, or to receive power or feedback signals from the pump device 100.

Furthermore, the control circuitry 240 may include one or more dedicated memory devices 242 that store executable software instructions for a processor 243 communicatively coupled to the control circuitry 240. The control circuitry 240 may include other components, such as sensors, that are electrically connected to the main processor board 242. For example, at least a portion of the occlusion detection system 250 can be electrically connected to the main processor board 242 via a flexible circuit substrate or one or more wires, as described in more detail below in connection with FIG. 9.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in one or more memory devices arranged in the controller circuitry 240.

In some optional embodiments, the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry or to download data from the controller circuitry. For example, historical data of medicine delivery can be downloaded from the controller circuitry 240 (via the cable connector) to a computer system of a physician or a user for purposes of analysis and program adjustments. Optionally, the data cable can also provide recharging power.

Figure 7:
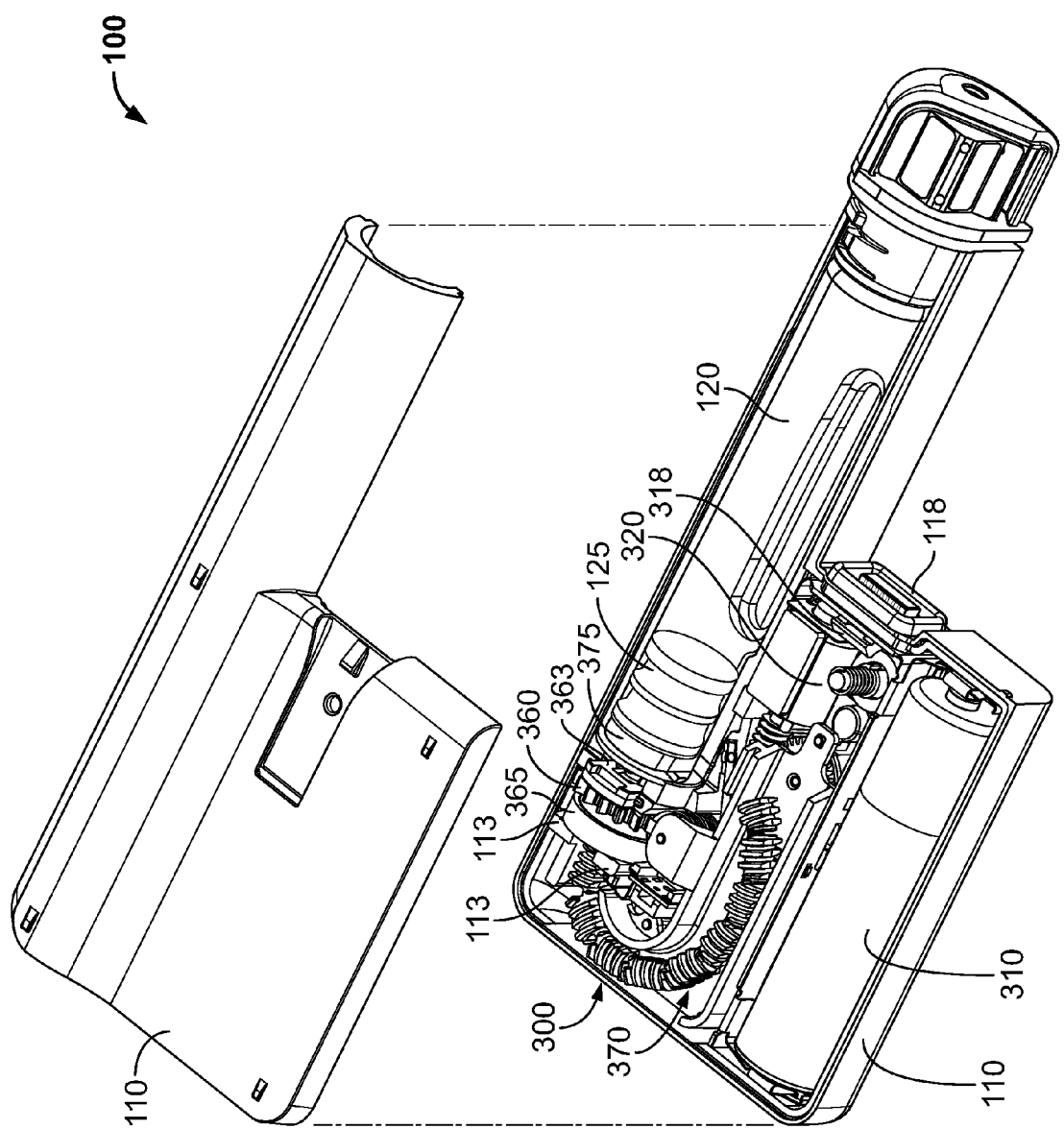
FIG. 7 is an exploded perspective view of a pump device for an infusion pump system, in accordance with some embodiments.

Referring now to FIG. 7, the pump device 100 can include a drive system 300 that is controlled by the controller device 200. In this embodiment, the drive system 300 can incrementally dispense fluid in a controlled manner from cartridge 120 inserted into the pump device 100. Also, the pump device 100 may include a connector circuit 318 to facilitate the transfer of signals to and from the electrical connector 118. In some implementations, the connector circuit 318 in the pump device 100 may include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connector circuit 318 can operate as a passageway to transmit electrical control signals from the controller circuitry 240 of the controller device 200 to the drive system 300. The connector circuit 318 can also operate as a passageway for the electrical power from a power source 310 housed in the pump device 300 to pass to the controller device 200 for recharging of the rechargeable battery 245. Furthermore, the connector circuit 318 can operate as a passageway for feedback signals from the drive system 300 to the controller circuitry 240 of the controller device 200.

In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 7, in some embodiment, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 375. In this embodiment, the reversible motor 320 drives a gear system to cause the rotation of the drive wheel 360 that is coupled with bearing 365. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 7, the drive wheel 360 is the driver while the flexible piston rod 370 is the driven member. As further described below, the rotation of the drive wheel 360 can drive the flexible piston rod 370 forward in a linear longitudinal direction.

Referring now to FIGS. 8-16, some embodiments of the occlusion detection system 250 can be configured to self-calibrate so as to reliably perform even when the pump system 10 is exposed to significant changes in environmental conditions, such as changes to the ambient temperature, pressure, or the like. In such circumstances, the occlusion detection system 250 can be used to provide reliable feedback to a user as to the occluded or non-occluded state of the medicine flow path. Further, the user interface 220 of the controller device 200 can be used to communicate an alarm to the user if an occlusion exists.

Figure 8:
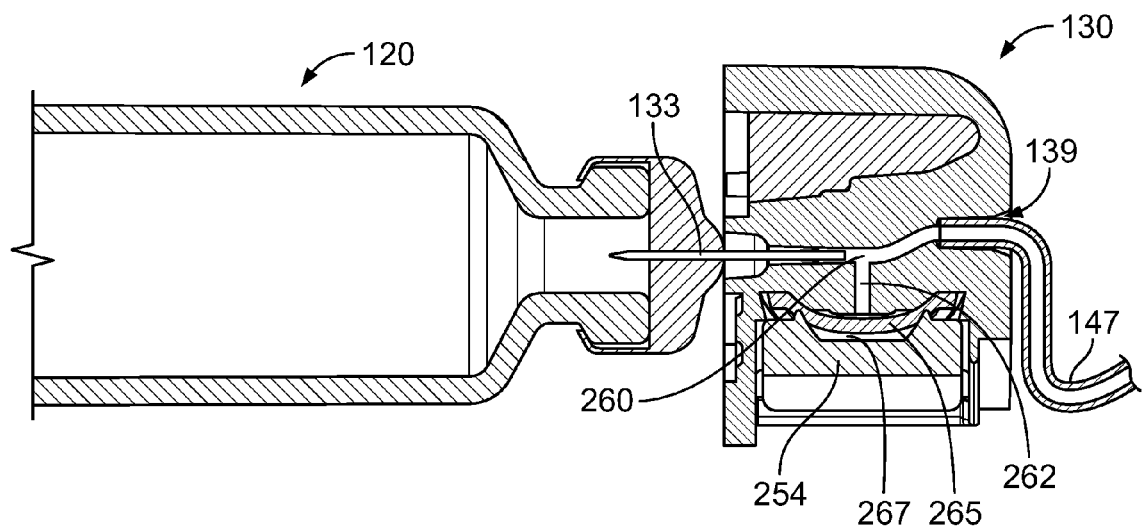
FIG. 8 is a cross-section view of the cap device and the medicine cartridge of FIG. 1.

Referring to FIG. 8, the cap device 130 can have a multi-piece construction that provides a flow path from the medicine container 120 to the infusion set tubing 147 (e.g., via an output port 139). At least a portion of the flow path through the cap device 130 may be monitored by the occlusion detection system 250 to determine if an occlusion exists downstream of the cap device 130 (e.g., if a kink or clog exists in the infusion set tubing 147 of cannula 149). The multi-piece construction of the cap device 130 can facilitate proper alignment of the cap device 130 and proper engagement with the medicine cartridge 120 during attachment of the cap device 130 to the pump housing 110. For example, during attachment of the cap device 130 to the pump housing, a needle penetrator 133 attached to a portion of the cap device can be advanced toward the septum of the medicine cartridge 120 to pierce the septum and open a fluid flow path. The flow path for the medicine that is dispensed from the medicine cartridge 120 can pass through the needle penetrator 133, through a fluid channel 260 (described below), through the infusion set tubing 147, and to the user.

The fluid channel 260 arranged in the cap device 130 may include a secondary channel 262 that extends to a flexible member 265. In this embodiment, one side of the flexible membrane 265 is exposed to the fluid channel 260 (via the secondary channel 262) while the opposite side of the flexible membrane 265 is adjacent to an air cavity 267 (also shown in FIGS. 12-14), which provides a volume into which the flexible membrane 265 can expand as pressure rises in the fluid channel 260. The flexible membrane 265 may comprise a flexible polymer material that bulges or otherwise deforms as the fluid pressure in the flow channel 260 rises and is preferably composed of silicon. As such, the flexible membrane 265 can flex into the air cavity 267 when the fluid pressure rises due to an occlusion in the flow path downstream of the fluid channel 260 (illustrated in reference to FIGS. 12-14).

Figure 9:
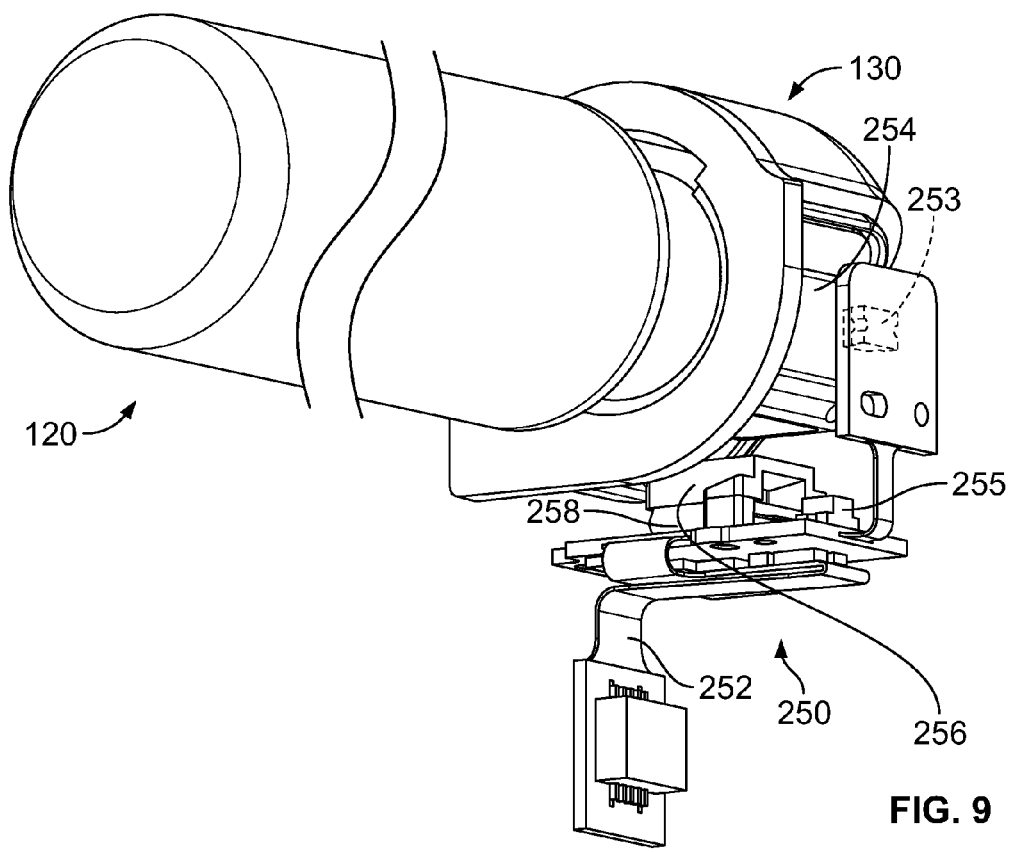
FIG. 9 is a perspective view of an alignment of the cap device and occlusion detection system, in accordance with some embodiments.

Referring to FIG. 9, the occlusion detection system 250 may include a number of components that are housed in the controller device 200. For example, the occlusion detection system 250 may include one or more light emitters and a light sensor arranged on the sensor circuit 252 that is housed by the controller device 200, thereby permitting these components to be reused along with the controller device (while the relatively low cost components in the pump device 100 are discarded after the "one time use" of the pump device 100). In a preferred embodiment, the sensor circuit 252 includes a primary light emitter 253, a reference light emitter 255, and a light sensor 258.

The sensor circuit 252 can be arranged so that the cap device 130 is aligned with the light emitters 253, 255 and the light sensor 258 when the pump device 100 is attached to the controller device 200. It should be understood that the pump housing 110 and the controller housing 210 have been removed from FIG. 9 for purposes of showing the relative position of the sensor circuit 252 (in the controller device 200 as shown in FIGS. 2 and 4) and the cap device 130 (attached to the pump housing 110 as shown in FIG. 2).

The sensor circuit 252 can be connected to the control circuitry 240 of the controller device 200 (FIG. 6) via a flexible circuit substrate or one or more wires. In a preferred embodiment, the sensor circuit 252 connects with the main processor board 242 via the flexible circuit substrate illustrated in FIG. 6. As such, the control circuitry 240 can receive sensor signals and employ detection software stored in one or more memory devices 242 to determine if an occlusion exists. If the sensor signals from the occlusion detection system 250 indicate that an occlusion exists in the fluid flow path, the controller device 200 can trigger an alert to inform the user. The alert may include a visual or audible alarm communicated via the user interface 220 of the controller device 200.

The light collector 256 can be made of any reflective material, preferably polished aluminum, and is designed to collect light from both the reference light emitter 255 and the primary light emitter 253. For example, apertures are advantageously constructed in the light collector 256 to allow light to reach the light sensor 258 from specific directions corresponding to light originating from the reference light emitter 255 and from the primary light emitter 253 (described below in connection with FIGS. 12-14).

In some embodiments, the reference light emitter 255 can provide a reference light reading at the sensor 258, which can be advantageously compared to a light reading from the primary light emitter 253 for purposes of determining when a reduced light reading from the main emitter 253 is caused by a buildup of fluid pressure in the fluid channel 260 (e.g., from an occlusion in the infusion set tubing 147) or is caused by some other reason not related to the presence of an occlusion (e.g., environmental conditions such as ambient temperature). For example, in some embodiments, the amount of light emitted from the primary emitter 253 begins to degrade or otherwise changes with fluctuations in ambient temperature and ambient light condition. If the control circuitry was configured to rely upon the light sensor readings detected by the light sensor 258 from the primary emitter 253 alone, such reductions in the amount of the light readings from the primary light emitter 253 would possibly induce false occlusion warnings (e.g., occlusion alerts where in fact the suboptimal temperatures are responsible for the reduced light readings and no occlusion is present in the infusion set tubing 147). In this embodiment, each of the primary emitter 253 and the reference light emitter 255 are substantially equally affected by the fluctuations in ambient temperature and ambient light condition. Accordingly, a comparison of the amount of the light received from the primary light emitter 253 with the amount of the light received from the reference light emitter 255 (rather than an absolute light measurement from the primary light emitter 253 alone) can be employed to substantially reduce or eliminate the number of false occlusion warnings.

Figure 10:
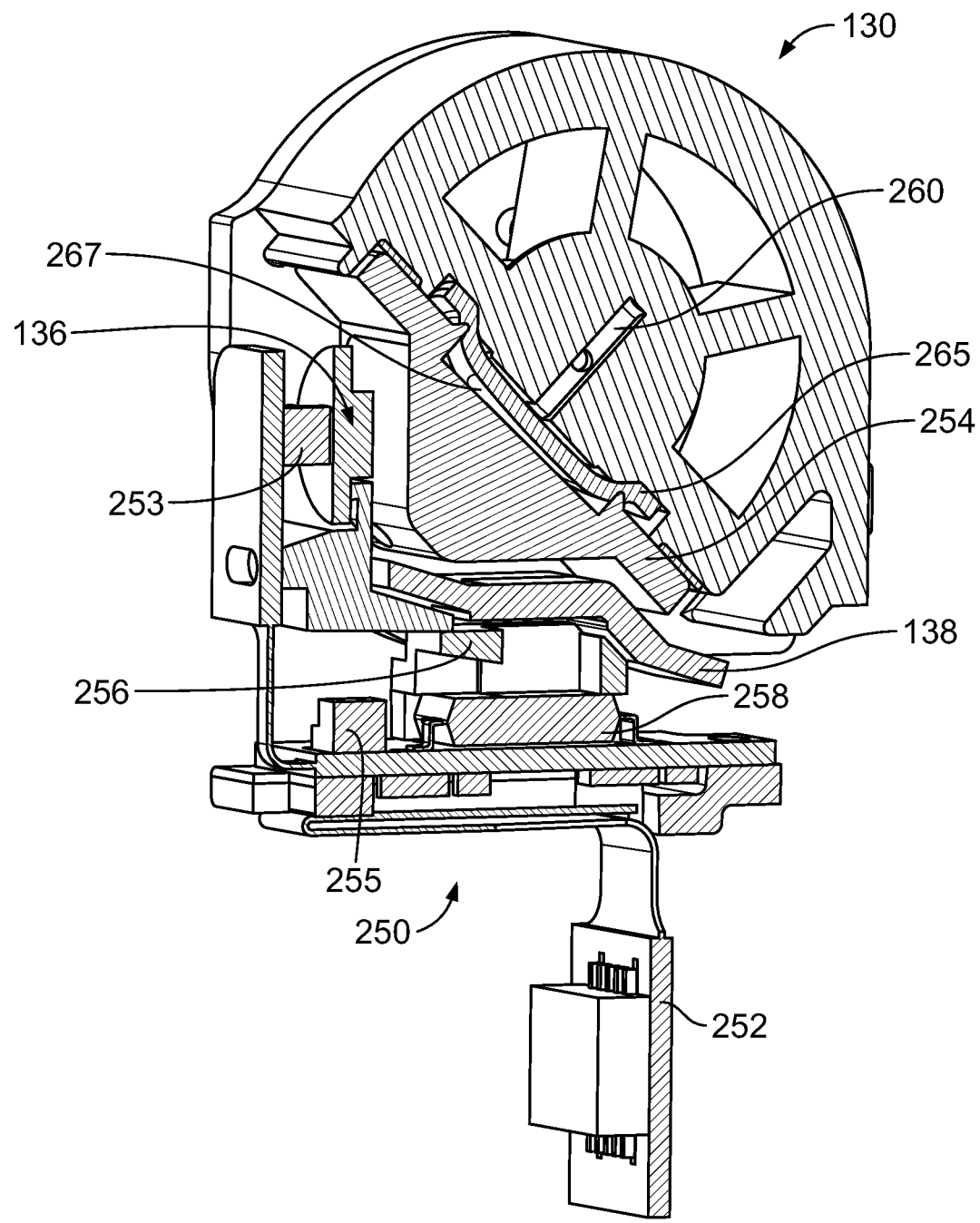
FIG. 10 is a cross-sectional perspective view of the alignment shown in FIG. 9.

Referring to FIG. 10, the sensor circuit 252 can be arranged so that the flexible membrane 265 and air gap 267 in the cap device 130 are aligned with the primary light emitter 253 and the light sensor 258 when the pump device 100 is attached to the controller device 200 (FIG. 2). Thus, when the infusion pump system 10 is preparing to dispense an incremental dosage of medicine, the primary light emitter 253 in the controller device 200 can direct light toward the flexible membrane 265 and air gap 267 in the cap device 130, and the light sensor 258 can receive light reflected from portions of the cap device 130. A cross-section through the cap device 130 and the controller device 200 illustrates one example of the alignment (although, here, the pump housing 110 and the controller housing 210 have been removed from FIG. 10 for purposes of better illustrating the alignment). It should be understood from the description herein that other alignment configurations can be implemented so that the light sensor 258 in the reusable controller device 200 is able to detect changes to fluid flow conditions in the pump device 100.

In the depicted embodiment, the sensor circuit 252 is arranged to at least partially extend to the barrel channel 211 (FIG. 2) of the controller device 200 so that the primary light emitter 253 and the light sensor 258 are positioned adjacent to the cap device 130. The light from the primary light emitter 253 can pass through one or more portions of the cap device 130 during its travel toward the flexible membrane 265 and air cavity 267 (shown in FIGS. 12-14). Accordingly, some portions of the cap device 130 may comprise a generally transparent material to permit light transmission therethrough. For example, the cap device may comprise a light transmissive member 254 that acts to transmit light from the primary light emitter 253 toward the flexible membrane 265 and air cavity 267, and in some cases, further acts to transmit reflected light toward the light sensor 258. Also, some portions of the controller housing 210 (FIG. 2) may include generally transparent material to permit light transmission therethrough. For example, in this embodiment, a first window component 136 of the controller housing 210 can include a generally transparent polymer material, which is positioned adjacent to the primary light emitter 253 so that the light from the primary emitter 253 is transmitted to the light transmissive member 254 of the cap device 130. Also, in this embodiment, a second window component 138 of the controller housing 210 is positioned adjacent to the light collector 256 and the light sensor 258. As such, when the pump device 100 is attached to the controller device 200, the second window component 138 is positioned between the light transmissive member 254 and the light sensor 258. Preferably, the remaining portion of the controller housing 210 that surrounds the reference light emitter 255 is generally opaque so that the light emitted from the reference light emitter 255 is prevented from passing to the light transmissive member 254 of the cap device 130. Such a construction may prevent or reduce the likelihood of inaccurate readings caused by light from the reference light emitter 255 interfering with the light emitted by the primary light emitter 253.

Still referring to FIG. 10, the internal light transmissive member 254 can be configured to receive light from the primary light emitter 253 and transmit at least a portion of that light toward the flexible membrane 265 and air cavity 267. In this embodiment, the internal light transmissive member 254 comprises a generally transparent polymer material that is capable of light transmission. As described in more detail below, the light that is transmitted in the light transmissive member 254 toward the fluid channel 260 can (in some circumstances) reflect from the interface where the internal light transmissive member 254 meets the air cavity 267. This reflected light can be further transmitted through the internal light transmissive member 254 to the light sensor 258.

Figure 11:
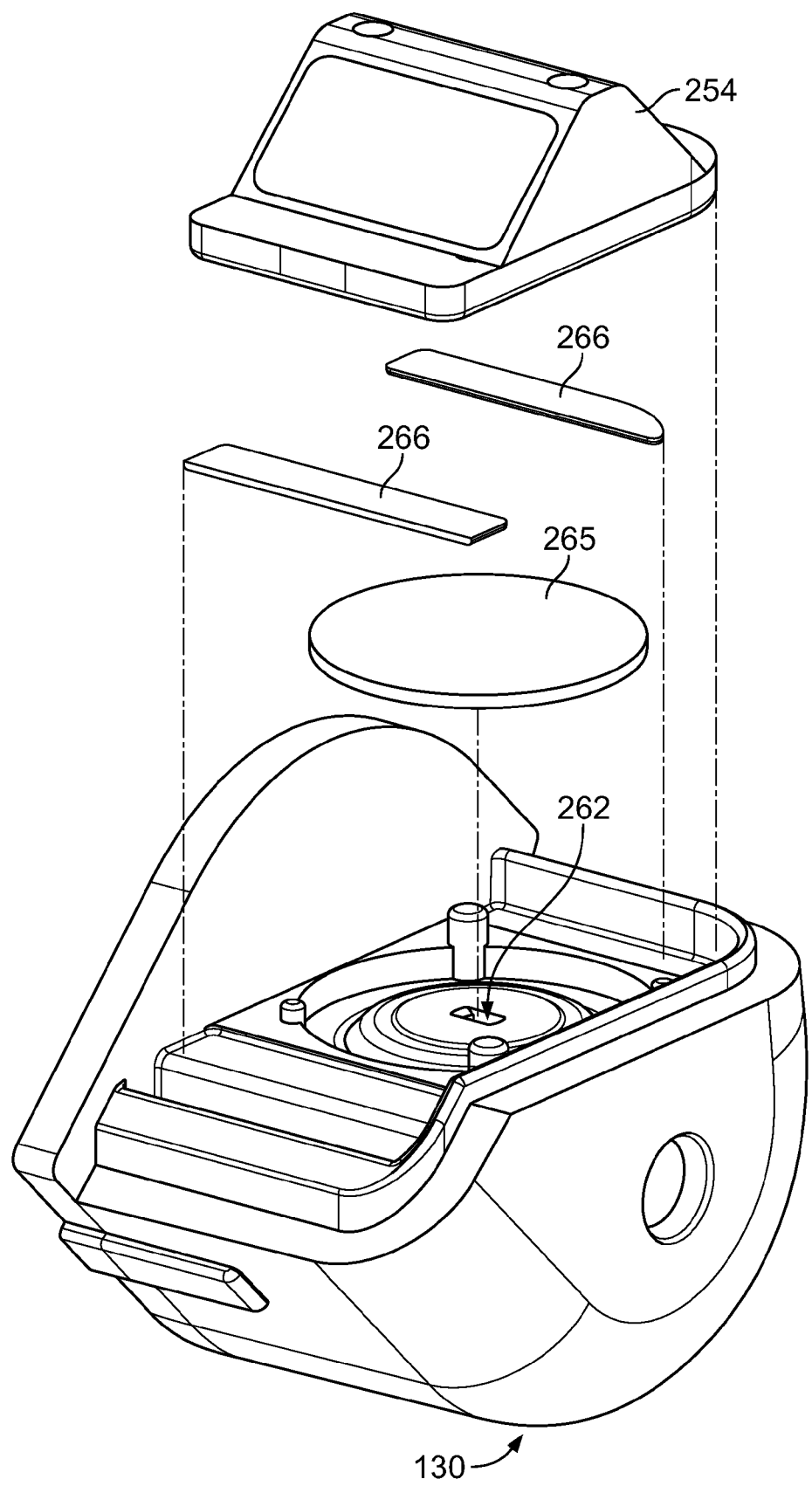
FIG. 11 is an exploded view of the cap device, in accordance with some embodiments.

Referring now to FIG. 11, the internal transmissive member 254 can be affixed to the remaining components of the cap device 130 using a bonding material 266, such as an adhesive film or glue. The flexible membrane 265 is positioned to form a seal between the fluid channel 262 and light transmissive member 254. That is, once the flexible membrane 265 is assembled into the cap device 130, the flexible membrane 265 deforms in response to a buildup of fluid pressure in the fluid path 260 (which is communicated via the secondary channel 262), but does not allow fluid in the fluid channel 260 to escape pass the membrane 265 into the air cavity 267 or otherwise interfere with other components of the pump device 100 or the controller device 200. This deformation of the flexible membrane 265 may change the size of the air cavity 267 (shown in FIGS. 12-14), which advantageously allows the light sensor to detect a change in the amount of the light emitted by the primary light emitter 253 indicating a possible occlusion of medicine flow path through the infusion set tubing 147 (FIGS. 3 and 8) which may prevent medicine from being delivered to the user.

Figure 12:
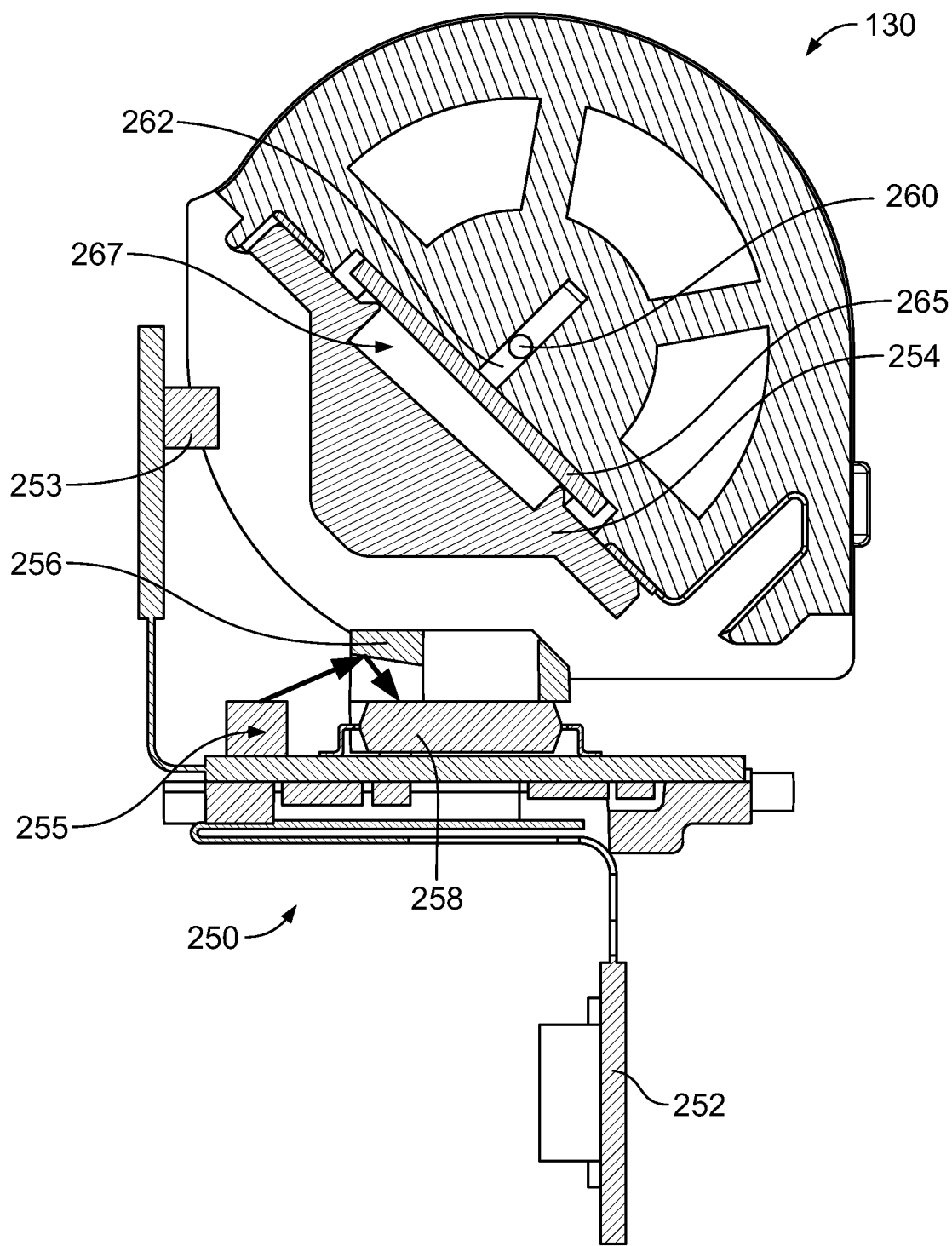
FIGS. 12-14 are cross-sectional views of the cap device and occlusion detection system, in accordance with some embodiments.
Figure 13:
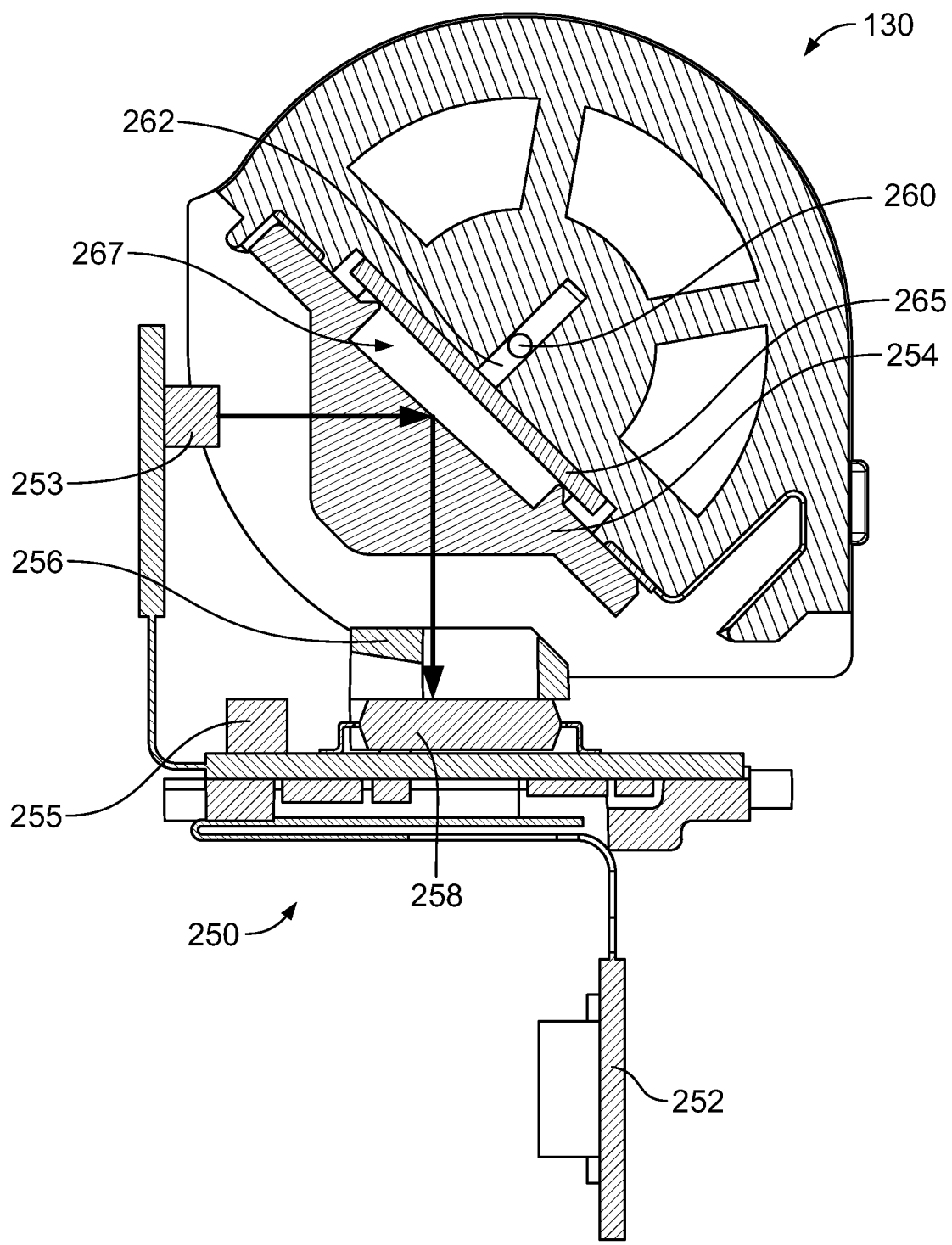
Figure 14:
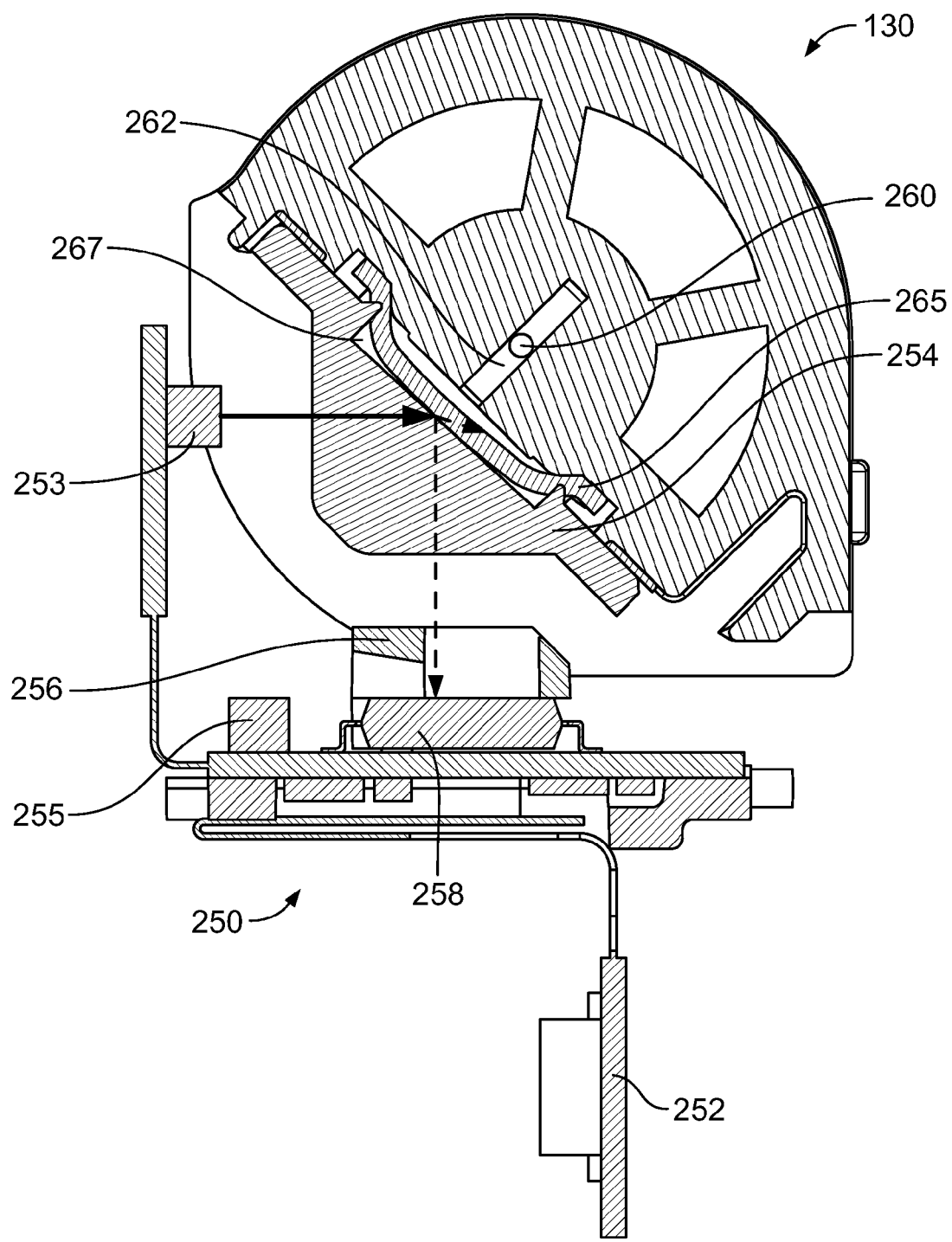

Referring now to FIGS. 12-14, the occlusion detection system 250 can be used to detect when an occlusion exists in the flow path from the pump device 100 to the user. For example, when an occlusion occurs in the infusion set tubing 146 or the infusion set tubing 147 (FIGS. 3 and 8), the delivery of medicine from the infusion pump system 10 to the user can be stopped or otherwise limited. If the user is unaware of the occlusion, the user may be deprived of the intended dosages of medicine from the infusion pump device for a period of time. Accordingly, the occlusion detection system 250 can be used to detect when such occlusions occur in the flow path to the user, and the controller device 200 can thereafter alert the user of the occlusion when particular conditions are met. The user may then inspect the pump device 100 or the infusion set 146 to eliminate the occlusion.

As shown in FIGS. 12-13, when no substantial occlusion exists in the flow path, the medicine can be dispensed under normal operating conditions from the medicine cartridge 120, through the cap device 130, and into the infusion tubing 147. In these normal operating conditions, the fluid pressure of the medicine passing through the cap device 130 may be below a selected threshold value. As such, the flexible membrane 265 that is adjacent to the fluid channel 260 is not substantially deformed (e.g., the membrane 265 does not flex downwardly into the air cavity 267 to abut the internal light transmissive member 254).

Referring to FIG. 12, in some embodiments, the occlusion sensor 250 may operate by activating the reference light emitter 255 in isolation from the primary light emitter 253. When the reference light emitter 255 is activated, the light is received by the light collector 256 and directed toward the light sensor 258 without passing through the light transmissive member 254 or any other portion of the cap device 130. For example, as shown in FIG. 12, at least a portion of the light from the reference emitter 255 (e.g., a wide-angle LED emitter in this embodiment) reflects off a surface of the light collector 256 and is received by the light sensor 258. As previously described, the generally opaque portion of the controller housing 210 (FIG. 2) may optionally prevent the light from the reference emitter 255 from passing outside the controller housing 210. Here, because the reference light emitter 255 does not transmit light through the light transmissive member 254, the amount of light transmitted by the reference light emitter 255 and received by the light sensor 258 is generally unaffected by a buildup of fluid pressure in the fluid channel 260 (as will be described in more detail in reference to FIGS. 13-14).

In other words, the amount of light emitted by the reference emitter 255 and received by the light sensor 258 does not fluctuate according to fluid pressure but may fluctuate according to other environmental factors, such as ambient temperature (and it should be understood that primary light emitter 253 is similarly affected by these same environmental factors). This configuration can be employed to aid in the detection of an occlusion that accounts for changes in environmental factors affecting the primary light emitter 253. For example, when the pump device 10 is operating in regions having lower ambient temperatures, both the reference light emitter 255 and the primary light emitter 253 will have reduced light outputs. In those circumstances, the occlusion detection system 250 can use the reduction in the amount of light from the reference light emitter 255 to account for the reduction in the amount of light from the primary light emitter 253. In other circumstances in which the light sensor 258 receives a reduced light signal only from the primary light emitter 253 while the light sensor 258 receive a normal light signal from the reference light emitter 255, then there is a greater likelihood of the presence of an occlusion and the user may be warned accordingly.

Referring to FIG. 13, when the medicine flow path is in a non-occluded state under normal operating circumstances, the light from the light emitter 253 can be reflected at the interface where the internal light transmissive member 254 meets the air cavity 267. In some embodiments, this light reflection may occur due to total internal reflection that the interface. Total internal reflection can occur in some circumstances when light passes through a first medium (e.g., the internal light transmissive member 254) and strikes an interface between the first medium and a second medium (e.g., the air cavity 267) at an angle greater than the critical angle. If the refractive index of the second medium (e.g., the air cavity 267) is lower than refractive index of the first medium (e.g., the internal light transmissive member 254), the light may undergo total internal reflection within the first medium.

For example, as shown in FIG. 13, the light emitter 253 can be an infrared light emitter that is directed toward the internal light transmissive member 254. The infrared light passes through the generally transparent first window 136 (shown in FIG. 10) and then transmits through the light transmissive member 254. In some embodiments, the surface of the light transmissive member 254 may be curved and may operate as a focusing lens that directs the infrared light toward the air cavity 267 proximate to the fluid channel 260, although a non-curved surface is shown for the embodiments of FIGS. 12-14.

Referring still to FIG. 13, when the medicine is dispensed under normal operating conditions, the flexible membrane 265 does not flex downwardly into the air cavity 267 to abut the internal light transmissive member 254. Accordingly, the infrared light passing through the internal light transmissive member 254 reflects at the interface where the internal light transmissive member 254 meets the air cavity 267. This reflected light continues through the internal light transmissive member 254 toward the light sensor 258. In this embodiment, the reflected light transmitted through the light transmissive member 254 passes through the second window 138 (shown in FIG. 10) and is subsequently received by the light collector 256 (described in reference to FIG. 9) and directed toward the light sensor 258. The light sensor 258 may comprise an infrared photo detector that is capable of converting the receipt of infrared light into electrical signals. These electrical signals from the light sensor 258 can be transmitted via the sensor circuit 252 to the control circuitry 240 (FIG. 6) for processing to determine if an occlusion alarm should be provided to the user.

Referring to FIG. 14, when an occlusion exists in the flow path, the fluid pressure of the medicine passing through the cap device 130 may rise to a level above the threshold value. For example, if pump device 100 attempts to dispense another incremental dosage of medicine when the infusion set tubing 147 is clogged or kinked, the fluid pressure upstream of the occlusion (e.g., in the medicine cartridge 120 and in the cap device 130) may be increased. In these circumstances, the flexible membrane 265 that is in fluid communication with the fluid channel 260 may be substantially deformed (e.g., the membrane 265 will flex downwardly into the air cavity 267 to abut the internal light transmissive member 254.)

The interface where the light transmissive member 254 meets the flexible membrane 265 (FIG. 14) provides different optical results than the previously described interface where the internal light transmissive member 254 meets the air cavity (FIG. 13). In particular, the amount of light from the light emitter 253 that is internally reflected at the interface where the internal light transmissive member 254 meets the flexible membrane 265 is measurably less (as illustrated by the dotted lines in FIG. 14). For example, none of the light or some other reduced portion of light from the light emitter 253 is internally reflected. (The light that is not internally reflected at this interface may pass into the medium of flexible membrane 265, for example.) If any portion of the light is internally reflected, this reduced portion of reflected light continues through the light transmissive member 254 toward the light sensor 258 (e.g., through second window 138 and received by collector 256). Because amount of light that is internally reflected in the light transmissive member 254 is measurably less, the light sensor 258 can produce detection signals that are different from those described in connection with FIG. 13. These detection signals may indicate that the fluid pressure in the cap device 130 has risen above a threshold level due to a downstream occlusion. These detection signals from the light sensor 258 (including signals detected from both the reference light emitter 255 and the primary light emitter 253) can be transmitted via the sensor circuit 252 to the control circuitry 240 (FIG. 6) for processing to determine if an occlusion alarm should be provided to the user.

Figure 15:
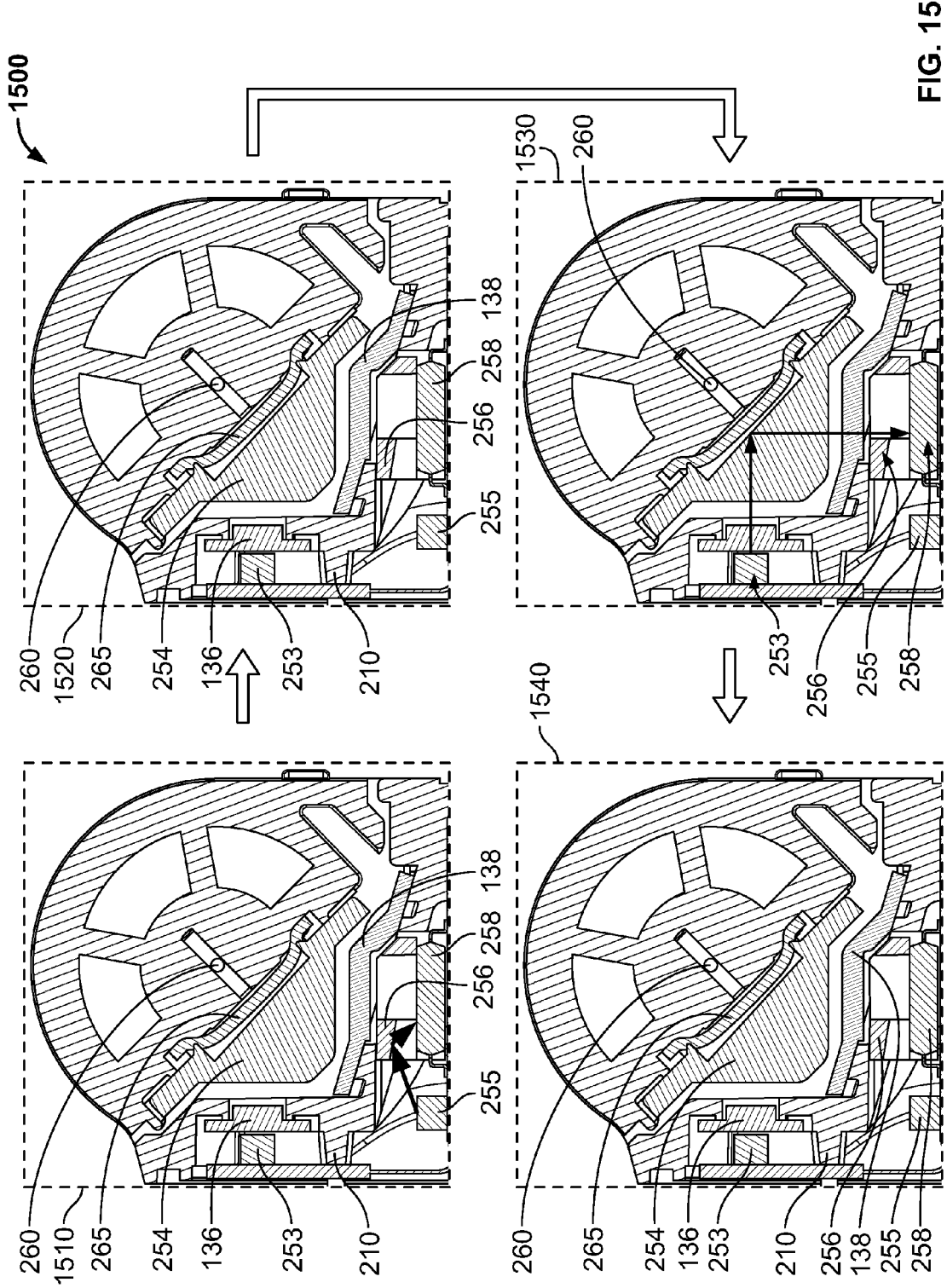
FIGS. 15-16 are a flow charts used to detect whether the infusion pump system is in an occluded or non-occluded state, in accordance with some embodiments.
Figure 16:
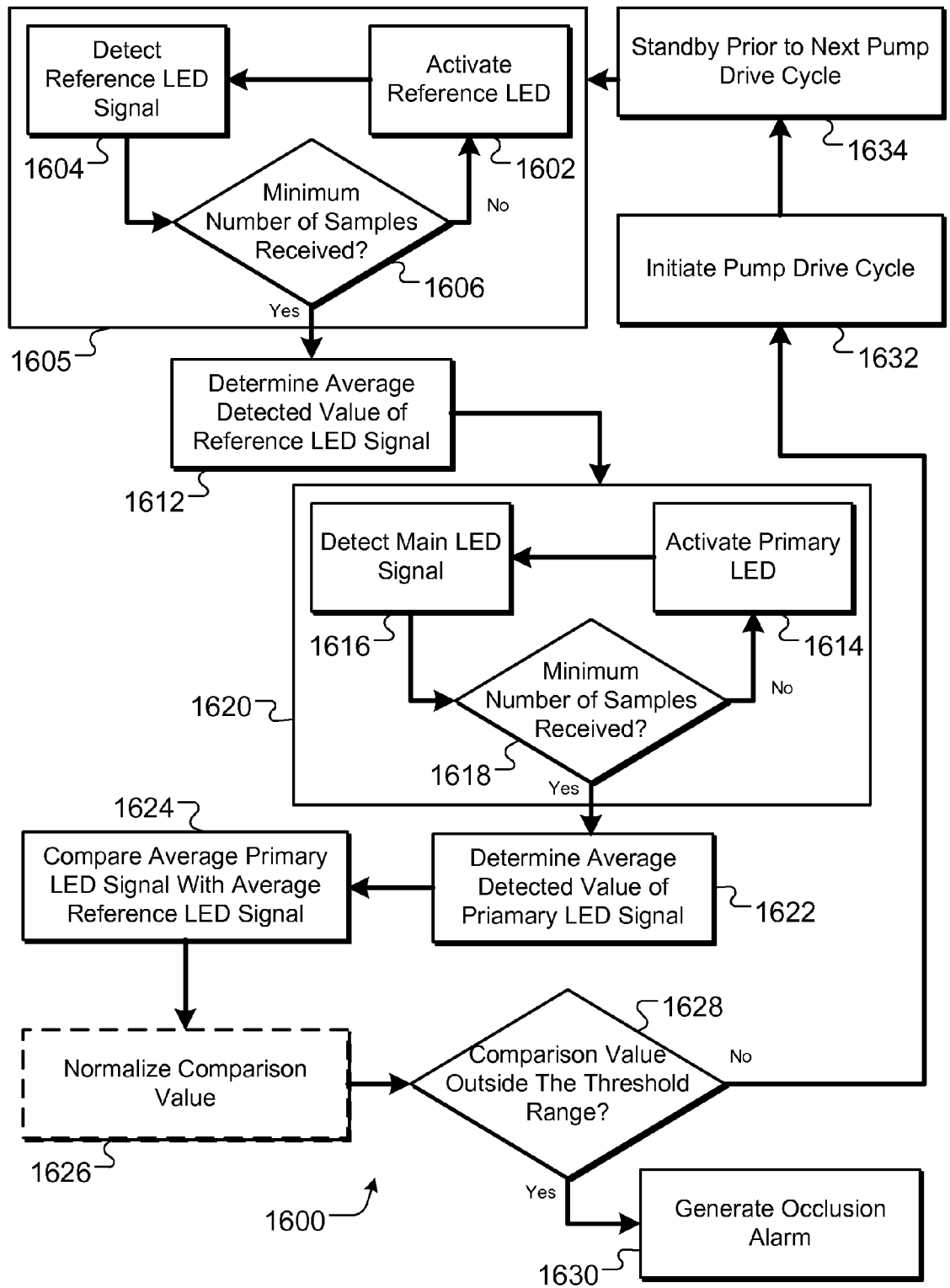

FIGS. 15-16 show processes 1500 and 1600, respectively, that can be performed for purposes of detecting the presence of an occlusion or non-occlusion in the medicine flow path to the pump user. In some embodiments, one or more of the steps described in reference to FIGS. 15-16 may be performed as part of another process. For example, the processes 1500 or 1600 may be performed when the pump device 100 is removably attached to the control device 200 to determine if the pump device 100 and control device 200 are correctly joined. Such a determination may occur in a number of circumstances, including when the pump device 100 and control device 200 are initially assembled after manufacture, or when a user discards a used pump device 100 and removably attaches a new pump device 100' (FIGS. 4-5). That is, the depicted processes 1500 or 1600 can be used to ensure that the cap device 130 is properly aligned with the occlusion detection system 250 (e.g., as shown in FIG. 9). In addition, processes 1500 or 1600 may be performed when a user manually clears an error message presented to the user by the control device 200. For example, by interacting with the user interface 220, the display device 222 and the one or more user-selectable buttons 224 (FIG. 1), the user can cancel an occlusion alarm and the control circuitry 240 may execute processes 1500 or 1600 in response. Also, in a preferred embodiment, processes 1500 or 1600 may be performed prior to each dispensation of medicine to the user to ensure that there are no occlusions in the medicine flow path to the pump user.

Furthermore, in a preferred embodiment, processes 1500 or 1600 may be performed initially to establish baseline light values used in subsequent executions of processes 1500 or 1600. For example, when the pump device 100 and control device 200 are removably attached or when a user cancels an occlusion alarm (e.g., displayed on displayed device 220), processes 1500 or 1600 may be performed to establish baseline values of light emitted by both the wide-angle reference light emitter 255 and the primary light emitter 253. These baseline values can be stored in one or more memory devices (e.g., on the circuit board 242) by the control circuitry 240 and can be used to determine the presence or absence of an occlusion. For example, if the value corresponding to the light emitted by the primary light emitter 253 is substantially less than the primary light emitter baseline value, an occlusion may exist if the value corresponding to the light emitted by the wide-angle reference light emitter 255 is substantially similar to the wide-angle reference light emitter baseline value. It should be understood that the processes 1500 and 1600 are illustrative of a preferred embodiment. As such, steps described may be performed in orders other than the one described herein.

Referring now to FIG. 15, some embodiments for the process 1500 for detecting the presence of an occlusion may include steps of activating the reference emitter 155 in isolation from the primary emitter 153. For example, as shown in the dashed box 1510, the control circuitry 240 may activate the reference light emitter 255 to emit light. This emitted light reflects off of the interior surface of the light collector 256 and is received by the light sensor 258. As previously described, the light collector 256 may include a polished interior surface that can redirect the light emitted by the wide-angle light emitter 255 onto the detecting surface of the light sensor 258. From there, the light sensor 258 can generate an electrical signal corresponding to the received light emission and these electrical signals can be used to determine the amount of emitted light. Optionally, as will be described in reference to FIG. 16, the step shown by dashed box 1510 may be repeatedly performed a number of times to advantageously reduce the effects of outlier sensor signals by implementing an averaging determination to obtain a more accurate measurement of the light emitted from the light emitter 255.

Still referring to FIG. 15, the process 1500 may include a step shown by dashed box 1520 in which the control circuitry 240 waits a predetermined period of time before activating the primary light emitter 253. For example, the control circuitry 240 may delay for about 0.1 seconds to about 0.9 seconds before activating the primary light emitter 253 (as illustrated by dashed box 1530). Optionally, during the delay period the control circuitry 240 may present an error message on the display device 222, alerting the user to the existence of an operating error. For example, a misalignment of the reference light emitter 255 with the cap device 130 may be detected when a baseline value is below some predetermined threshold. As shown in the dashed box 1530, the control circuitry 240 may then activate the primary light emitter 253. When the medicine flow path is in an non-occluded state, the emitted light travels through the light transmissive member 254 (FIGS. 13-14) and is reflected toward the light sensor 258. As previously described, the reflected light may pass through the light transmissive member 254, and some or all of the light may reflect from the interface where the internal light transmissive member 254 meets the air cavity 267 (FIG. 10). Then, the reflected light may pass through the second window 138 (FIG. 9), the light collector 256 (FIG. 9), and reach the light sensor 258. As described in reference to FIGS. 13-14, the amount of light reaching the light sensor 258 may be indicative of the presence or absence of an occlusion. For example, in some operational circumstances, a reduced electrical signal (relative to previously received electrical signals) received by the control circuitry 240 may indicate the presence of an occlusion or the presence of suboptimal ambient temperature. Conversely, in some operational circumstance, an electrical signal similar to previously received electrical signals (e.g., determined according to multiple executions of processes 1500 or 1600), may indicate the absence of an occlusion or the presence of optimal ambient temperature.

Still referring to FIG. 15, as shown by dashed box 1540, the control circuitry 240 can wait a predetermined period of time. For example, the control circuitry 240 may wait on the order of about 0.1 seconds to about 0.9 seconds before activating the drive system 300 of the pump device 100 to dispense the next dosage of medicine. Optionally, in this embodiment, during the delay period the control circuitry 240 determines the average light emitted by the primary light emitter 253 corresponding to the one or more electrical signals received by the control circuitry 240 as communicated by the light sensor 258. In addition, during the delay period the control circuitry 240 may determine the presence or absence of an occlusion by comparing the light detected from the primary light emitter 253 to the light detected from the reference light emitter 255. In response to the determination of a possible occlusion, the control circuitry 240 may activate the control device 200 to display an alert message on the display device 222 while foregoing the next incremental dosage of medicine.

Referring now to FIG. 16, the control circuitry 240 may implement a process 1600 to determine whether the medicine flow path is in an occluded or non-occluded state. The process 1600 may be at least partially implemented in an occlusion detection software algorithm that is stored on a memory device and executed by a processor of the control circuitry. In this embodiment, the control circuitry 240 may implement a first iterative step shown by box 1605 so to activate the wide-angle reference light emitter 255 to turn on in step 1602. For example, because the control circuitry 240 is in electrical communication with the reference light emitter 255, the control circuitry 240 can generate an electrical signal that when received by the wide-angle reference light emitter 255 causes the wide-angle light emitter 255 to emit light. In addition, the absence of the electrical signal may cause the reference light emitter 255 to deactivate.

In a step shown by box 1604, the control circuitry 240 detects a signal corresponding to the light emitted by the reference light emitter 255 and received by the light sensor 258. For example, light transmitted from the reference light emitter 255 may reflect off of the interior surface of the light collector 256 and interact with the light sensor 258. As described in more detail above, the light sensor 258 can generate an electrical signal corresponding to the received light. Because the control circuitry 240 is in electrical communication with the light sensor 258, the control circuitry 240 detects the signal corresponding to the light emitted by the wide-angle reference light emitter 255 when the control circuitry 240 receives the electrical signal from the light sensor 258. In a preferred embodiment, each of the detected signals corresponding to light emitted by the reference light emitter 255 is a floating point value within the range of [0-1] and is stored on one more dedicated memory devices included in the control circuitry 240.

In a decision shown by step 1606, the control circuitry 240 determines whether a minimum number of light samples transmitted by the wide-angle light emitter 255 has been received. For example, in a preferred embodiment, the control circuitry 240 determines whether sixteen iterations of activating the reference emitter 255 and detecting the corresponding sixteen electrical signals from the light sensor 258 have been completed. If the minimum number of light samples has not been received, than the control circuitry 240 may instruct the reference light emitter 255 to activate again, repeating the steps included in the first iterative step shown by box 1605. In this embodiment, the sixteen iterations can be consecutive performed in a period of 0.5 seconds or less.

Once the minimum number of light samples has been received (e.g., sixteen in this embodiment), the control circuitry 240 may perform operation 1612 to determine an average detected value of the reference light emitter samples received. For example, in a preferred embodiment, because the control circuitry 240 receives sixteen light samples from the reference light emitter 255, the sixteen light samples are added together and the total divided by sixteen to determine the average detected value of the wide-angle reference samples received. In a preferred embodiment, the determined average value corresponding to light transmitted by the reference light emitter 255 is a floating point value within the range of [0-1] and is stored on one or more dedicated memory devices included in the control circuitry 240.

In a second iterative step shown by box 1620, the control circuitry 240 activates the primary light emitter 253 as shown in a step 1614. For example, because the control circuitry 240 is in electrical communication with the primary light emitter 253, the control circuitry 240 can generate an electrical signal that when received by the primary light emitter 253 activates the primary light emitter 253 to emit light. In addition, the absence of the electrical signal may instruct the primary light emitter 253 to deactivate.

In a step 1616, the control circuitry 240 can detect a signal corresponding to the light emitted by the primary light emitter 253 and received at the light sensor 258. For example, the light transmitted from the primary light emitter 253 that passes through the light transmissive member 254, may be reflected by the interface between the light transmissive member 254 and the air cavity 267 toward the light sensor 258. As described in more detail above, the light sensor 258 can generate an electrical signal corresponding to the received light. Because the control circuitry 240 is in electrical communication with the light sensor 258, the control circuitry 240 detects the signal corresponding to the light emitted by the primary light emitter 253 when the control circuitry 240 receives the electrical signal from the light sensor 258. In a preferred embodiment, each of the detected signals corresponding to the light emitted by the primary light emitter 253 is a floating point value within the range of [0-1] and is stored on one more dedicated memory devices included in the control circuitry 240.

Still referring to FIG. 16, the process may continue to a decision shown by box 1618, in which the control circuitry 240 determines whether a minimum number of light samples transmitted by the primary light emitter 253 has been received. For example, in a preferred embodiment, the control circuitry 240 determines whether sixteen iterations of activating the primary emitter 253 and detecting the corresponding sixteen electrical signals from the light sensor 258 have been completed. If the minimum number of light samples has not been received, than the control circuitry 240 may activate the primary light emitter 253 again, thereby repeating the steps included in the second iterative step shown by box 1620.

Once the minimum number of light samples has been received, in a step shown by box 1622, the control circuitry 240 determines an average detected value of the primary light emitter samples received. For example, in a preferred embodiment, because the control circuitry 240 receives 16 light samples from the primary light emitter 253, the 16 light samples are added together and the total divided by 16 to determine the average detected value of the primary light emitter samples received. In a preferred embodiment, the determined average value corresponding to light transmitted by the primary light emitter 253 is a floating point value within the range of [0-1] and is stored on one or more dedicated memory devices included in the control circuitry 240.

The process 1600 for to determining whether the medicine flow path is in an occluded or non-occluded state may include an operation that compares the detected value of the light emitted by the primary light emitter 253 with the detected value of the light emitted by the reference light emitter 253. For example, in this embodiment, the step 1624 indicates that the control circuitry 240 compares the average detected value of the light emitted by the primary light emitter 253 (determined by the step shown by box 1622) with the average detected value of the light emitted by the wide-angle reference light emitter 253 (determined by the step shown by box 1612). In one example of this comparison function, the average detected value of the light emitted by the primary light emitter 253 is divided by the average detected value of the light emitted by the wide-angle reference light emitter 255. Also, in particular embodiments, the resulting comparison value is a floating point value within the range of [0-1] and is stored on one more dedicated memory devices included in the control circuitry 240.

In an optional step shown by dashed box 1626, the control circuitry 240 normalized the comparison value determined in the step shown by box 1624. For example, in a preferred embodiment, the floating point comparison value in the range of [0-1] is multiplied by 100, normalizing the comparison value to an integer value in the range of [0-100].

The process 1600 may use the comparison value as an indicator of whether the medicine flow path is in an occluded or non-occluded state. For example, in this embodiment, the process 1600 includes a step 1628 in which the control circuitry 240 determines if the comparison value (e.g., either of the values determined by the step shown by box 1624 or the normalized comparison value determined in the step shown by box 1626) is outside a threshold range (e.g., less than or equal to a minimum threshold value, or greater than or equal to a maximum threshold value, or the like).

In particular embodiments, this step 1628 may employ a baseline value, which can be initially calculated when the pump device 100 is initially primed to force medicine through the infusion set tubing 147 (e.g., when there are no blockages or kinks and the medicine is visibly moved out of the tubing 147). In some cases, the baseline value can be calculated by the control circuitry 240 as a value corresponding to an initial amount of detected light from the primary light emitter 253 during or immediately before the priming operation divided by a value corresponding to a initial amount of light emitted by the reference light emitter 255 during or immediately before the priming operation).

In this embodiment of step 1628, the normalized comparison value (e.g., from step 1626) is divided by this previously determined baseline value. In a preferred embodiment, if this comparison is less than or equal to a minimum threshold value (such as 40% in this embodiment), then the comparison is outside the threshold range. In other words, for this particular embodiment, the comparison value is outside the threshold range when:

$(M_D/R_D)/(M_B/R_B)$ is less than or equal to 40%, where $M_D$ is the averaged value of the detected light values from the primary light emitter 253 determined in the step shown by box 1612, $R_D$ is the averaged value of the detected light values from the reference light emitter 255 determined in the step shown by box 1622, $M_B$ is the averaged value of the detected baseline values from the primary light emitter 253 (e.g., recorded and stored by the control circuitry 240 during or immediately before the initial priming operation for the pump device), and $R_B$ is averaged value of the detected baseline values from the reference light emitter 255 (e.g., recorded and stored by the control circuitry 240 during or immediately before the initial priming operation for the pump device).

It should be understood from the description herein that the minimum threshold value can be a value other than 40%. For example, in other embodiments, the minimum threshold value can be implemented in the occlusion detection software as a value selected from the range of about 10% to about 70%, about 20% to about 60%, and preferably about 30% to about 50%.

Optionally, in some embodiments, the control circuitry 240 stores a set of the most recently calculated comparison values from step 1628. This set of recent comparison values from step 1628 can be employed by the occlusion detection software of the control circuitry 240 to determine if there is a trend that is indicative of an ongoing occlusion in the medicine flow path. For example, if a plurality of consecutive values from the comparison step 1628 are all less than or equal to the minimum threshold value (such as 40% in this embodiment), occlusion detection software of the control circuitry 240 may determine that an occlusion exists and a user alert should be output. In this particular embodiment, the control circuitry 240 stores at least five of the most recent comparison values from the step 1628. In such embodiments, when the most recent five comparison values from the step 1628 are outside the threshold range, then the control circuitry 240 will generate an occlusion alarm in a step shown by box 1630. Alternatively, the control circuitry 240 may not necessarily store a plurality of the most recently calculated comparison values from step 1628, but instead may generate the occlusion alarm in step 1630 after any one instance of the comparison value from step 1628 are outside the threshold range.

The process 1600 can be performed immediately prior to each drive cycle of the pump device 100. In such circumstances, the process may proceed to step 1632 in which the pump drive cycle is initiate if the comparison value from step 1628 is not outside the threshold range (or, in a preferred embodiment, if one of the five most recent comparison values is not outside the threshold range). For example, if the comparison step 1628 reveals that $(M_D/R_D)/(M_B/R_B)$ is greater than 40%, this result is an indication that there is no meaningful occlusion in the medicine flow path and the control circuitry 240 may then initiate the pump drive cycle 1632. When the control circuitry 240 initiates the pump drive cycle in step 1632 (e.g., in accordance with a previously determined basal dosage schedule or a requested bolus dosage), the pump drive system 300 is activated to dispense the dose of medicine through the infusion tubing 147 into the infusion set 146 and cannula 149. After the pump drive cycle 1632 is activated, the control circuitry may then standby 1634 prior to the next pump drive cycle (e.g., in accordance with a previously determined basal dosage schedule or a requested bolus dosage) before executing process 1600 again.

A number of embodiments of the invention have been described. Nevertheless, it will be understood that various modifications may be made without departing from the spirit and scope of the invention. Accordingly, other embodiments are within the scope of the following claims.

What is claimed is:

1. A method for detecting an occlusion in a flow path from an infusion pump system, comprising:
   activating a reference light emitter to direct light toward a light sensor housed in an infusion pump system, wherein the light sensor generates an electrical signal in response to receiving light from the reference light emitter;
   determining a first value indicative of light detected at the light sensor from the reference light emitter;
   activating a primary light emitter to direct light toward a medicine flow path for the infusion pump system, the medicine flow path comprising a flexible membrane in fluid communication with a fluid channel that at least partially defines an insulin flow path between an insulin reservoir and an output port, wherein a fluid pressure in the fluid channel acts upon the flexible membrane, wherein the light sensor receives a least a portion of the light emitted from the primary light emitter, wherein the light sensor receives light from the primary light emitter that is internally reflected by a light transmissive member, the light transmissive member having two generally flat surfaces through which the light from the primary light emitter enters and exits the light transmissive member, the medicine flow path further comprising an air cavity positioned adjacent to the flexible membrane and generally opposite the fluid channel, wherein the light transmissive member is adjacent to the air cavity, wherein the reference light emitter is spaced apart from the primary light emitter such that the light emitted from the reference light emitter is received by the light sensor without being directed towards the flexible membrane or passing through the light transmissive member;
   determining a second value indicative of light detected at the light sensor from the primary light emitter; and
   determining if a fluid pressure in the fluid channel exceeds a threshold value based at least in part on a comparison of the second value to the first value; and
   providing feedback regarding the occluded or non-occluded state of the medicine flow path.

2. The method of claim 1, wherein a control circuitry activates the primary light emitter in isolation from activation of the reference light emitter.

3. The method of claim 2, wherein the control circuitry electrically is connected to the primary light emitter, the reference light emitter, and the light sensor.

4. The method of claim 2, wherein the control circuitry determines the fluid pressure.

5. The method of claim 1, wherein the feedback comprises an occlusion alarm.

6. The method of claim 5, wherein the occlusion alarm is generated by the infusion pump system.

7. The method of claim 1, wherein the light transmissive member is arranged opposite the flexible membrane such that fluid pressure in the fluid channel above a threshold value causes the flexible membrane to deform into the air cavity and toward the light transmissive member.

8. The method of claim 7, wherein the primary light emitter is configured to align with the light transmissive member and emit light into the light transmissive member; wherein the light sensor is configured to align with the light transmissive member and receive light from the primary light emitter that passes through the light transmissive member; and wherein the reference light emitter configured to emit light that is received by the light sensor, wherein the reference light emitter is spaced apart from the primary light emitter.

9. The method of claim 8, wherein when the flexible membrane is in a non-abutting position with the light transmissive member, the light from the light emitter undergoes total internal reflection within the light transmissive member at an interface with the air cavity.

10. The method of claim 9, wherein in response to a pressure in a flow path extending from the fluid channel exceeding a threshold, the flexible membrane expands to abut the light transmissive member.

11. The method of claim 10, wherein when the flexible membrane abuts the light transmissive member, at least a portion the light from the primary light emitter passes from the light transmissive member and into the flexible membrane at an interface between the light transmissive member and the flexible membrane.

12. The method of claim 8, wherein the light sensor, the primary light emitter, and the reference light emitter are housed in a reusable controller device while the flexible membrane, the air cavity, and the light transmissive member are components of a cap device that attaches to a disposable pump device configured to removably attach to the reusable controller device.

* * * * *

UNITED STATES PATENT AND TRADEMARK OFFICE
CERTIFICATE OF CORRECTION

PATENT NO.      : 9,610,404 B2
APPLICATION NO. : 14/461678
DATED           : April 4, 2017
INVENTOR(S)     : Yaron Rotstein Page 1 of 1

It is certified that error appears in the above-identified patent and that said Letters Patent is hereby corrected as shown below:

In the Claims

Column 24, Line 32: In Claim 8, after "emitter" insert -- is --.

Column 24, Line 41: In Claim 10, delete "to a" and insert -- to the --, therefor.

Column 24, Line 42: In Claim 10, delete "in a" and insert -- in the --, therefor.

Column 24, Line 43: In Claim 10, delete "exceeding a" and insert -- exceeding the --, therefor.

Signed and Sealed this
Twenty-third Day of May, 2017

Michelle K. Lee
*Director of the United States Patent and Trademark Office*